US011103273B2

(12) United States Patent
Kakony (10) Patent No.: US 11,103,273 B2
(45) Date of Patent: Aug. 31, 2021

(54) POWERED HAIR RESTORATION AND SURGICAL ASSEMBLY (71) Applicant: Rasim Kakony, Glenview, IL (US)

(72) Inventor: Rasim Kakony, Glenview, IL (US)

(*) Notice: Subject to any disclaimer, the term of this patent is extended or adjusted under 35 U.S.C. 154(b) by 290 days.

(21) Appl. No.: 16/220,168

(22) Filed: Dec. 14, 2018

(65) Prior Publication Data
US 2020/0187973 A1 Jun. 18, 2020

(51) Int. Cl.
A61B 17/32 (2006.01)
A61B 17/3205 (2006.01)
A61B 17/34 (2006.01)
A61B 17/3209 (2006.01)
A61B 17/00 (2006.01)
A61F 2/10 (2006.01)

(52) U.S. Cl.
CPC .. *A61B 17/32053* (2013.01); *A61B 17/32093* (2013.01); *A61B 17/3468* (2013.01); *A61B 2017/00115* (2013.01); *A61B 2017/00752* (2013.01); *A61B 2017/320044* (2013.01); *A61F 2/10* (2013.01)

(58) Field of Classification Search
CPC .......... A61B 17/3203; A61B 17/32053; A61B 2017/00752; A61B 2017/320044; A61B 17/32093; A61B 2017/00115
See application file for complete search history.

(56) References Cited

U.S. PATENT DOCUMENTS

| 5,782,853 A | 7/1998 | Zeevi |
| 5,913,857 A * | 6/1999 | Ritchart ............. A61B 18/1482 604/22 |
| 6,221,088 B1 | 4/2001 | Bays |
| 6,332,891 B1 * | 12/2001 | Himes .................... A61B 90/36 606/130 |
| 6,432,118 B1 | 8/2002 | Messerly |
| D568,475 S | 5/2008 | Sandel |
| 8,715,245 B2 | 5/2014 | Teufelberger |
| 8,998,931 B2 | 4/2015 | Wesley |
| 2007/0055173 A1 * | 3/2007 | DeLonzor .......... A61B 10/0266 600/564 |

(Continued)

FOREIGN PATENT DOCUMENTS

WO WO0124714 4/2001

*Primary Examiner* — Alexander J Orkin (57) ABSTRACT

An powered hair restoration and surgical assembly includes a housing for gripping during a surgical procedure. A blunt dissector is removably coupled to the housing for manipulating an incision. A control circuit is positioned in the housing and an incising unit is movably positioned in the housing. The incising unit is electrically coupled to the control circuit. The incising unit is extendable outwardly through the blunt dissector to incise skin on a patient and the incising unit is retractable into the blunt dissector. A fluid dispenser unit is positioned in the housing and the fluid dispenser unit is electrically coupled to the control circuit. The fluid dispenser unit is in fluid communication with the incising unit to deliver a selectable volume of the fluid into the incision when the incising unit is extended outwardly through the blunt dissector. A control is positioned on the housing. The control is electrically coupled to the control circuit for controlling operational parameters of the incising unit and the fluid dispenser unit.

1 Claim, 5 Drawing Sheets (56) References Cited

U.S. PATENT DOCUMENTS

| | | | |
|---|---|---|---|
| 2008/0177287 A1* | 7/2008 | Rassman | A61B 17/32053 606/133 |
| 2008/0300611 A1* | 12/2008 | Houser | A61B 17/320068 606/167 |
| 2009/0240261 A1* | 9/2009 | Drews | A61B 34/30 606/133 |
| 2012/0184969 A1* | 7/2012 | Melendez | A61B 17/3468 606/133 |
| 2015/0289624 A1 | 10/2015 | Abdullah | |

* cited by examiner

POWERED HAIR RESTORATION AND SURGICAL ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to surgical devices and more particularly pertains to a new surgical device for making incisions of a precise depth and length, and releasing a selected fluid during restorative hair surgical procedures.

BRIEF SUMMARY OF THE INVENTION

An embodiment of the disclosure meets the needs presented above by generally comprising a housing for gripping during a hair restoration surgical procedure. A blunt dissector is removably coupled to the housing for manipulating an incision. A control circuit is positioned in the housing and an incising unit is movably positioned in the housing. The incising unit is electrically coupled to the control circuit. The incising unit is extendable outwardly through the blunt dissector to incise skin on a patient and the incising unit is retractable into the blunt dissector. A fluid dispenser unit is positioned in the housing and the fluid dispenser unit is electrically coupled to the control circuit. The fluid dispenser unit is in fluid communication with the incising unit to deliver a selectable volume of the fluid into the incision when the incising unit is extended outwardly through the blunt dissector. A control is positioned on the housing and the control is electrically coupled to the control circuit for controlling operational parameters of the incising unit and the fluid dispenser unit.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
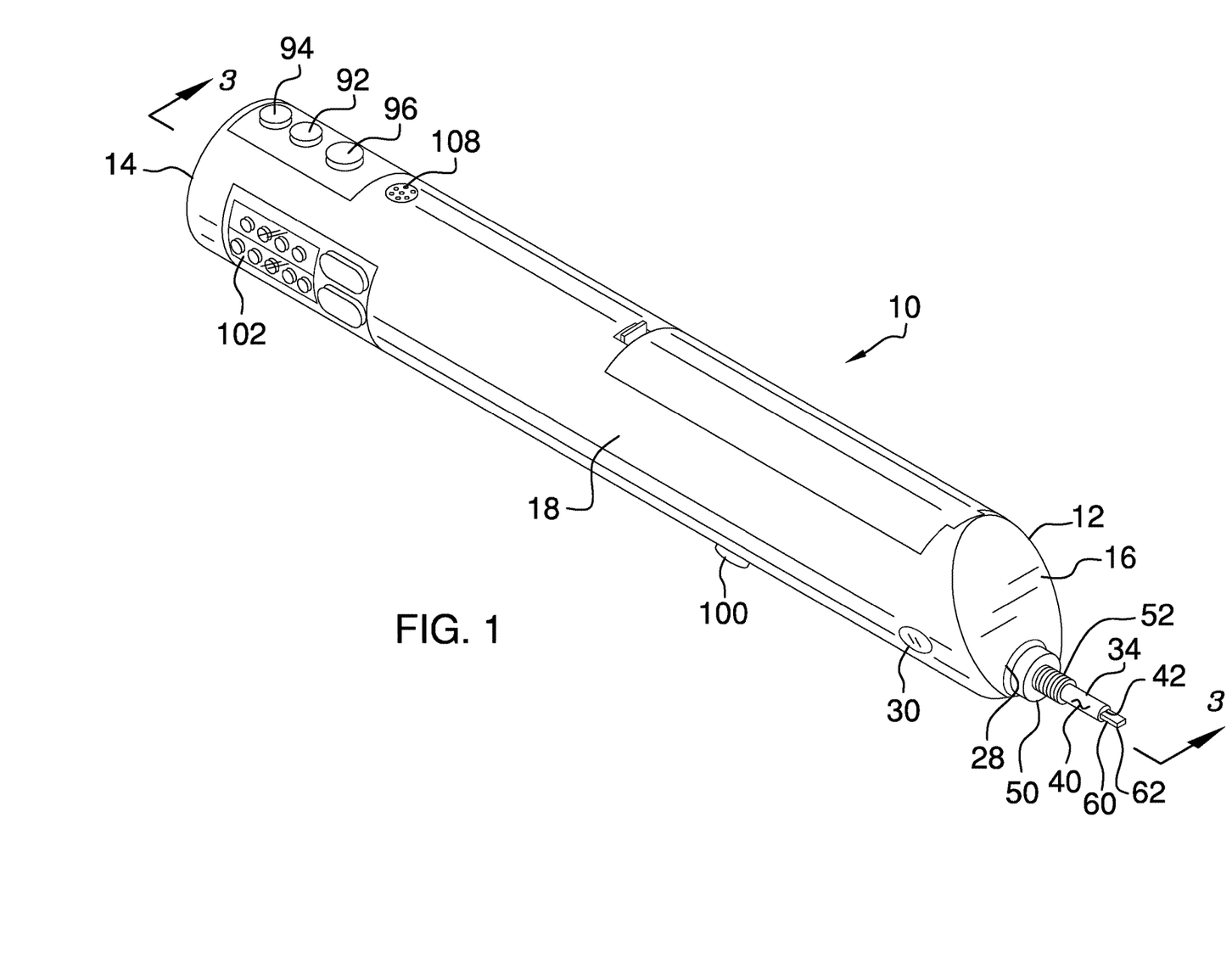
FIG. 1 is a perspective view of a powered hair restoration and surgical assembly according to an embodiment of the disclosure.
Figure 2:
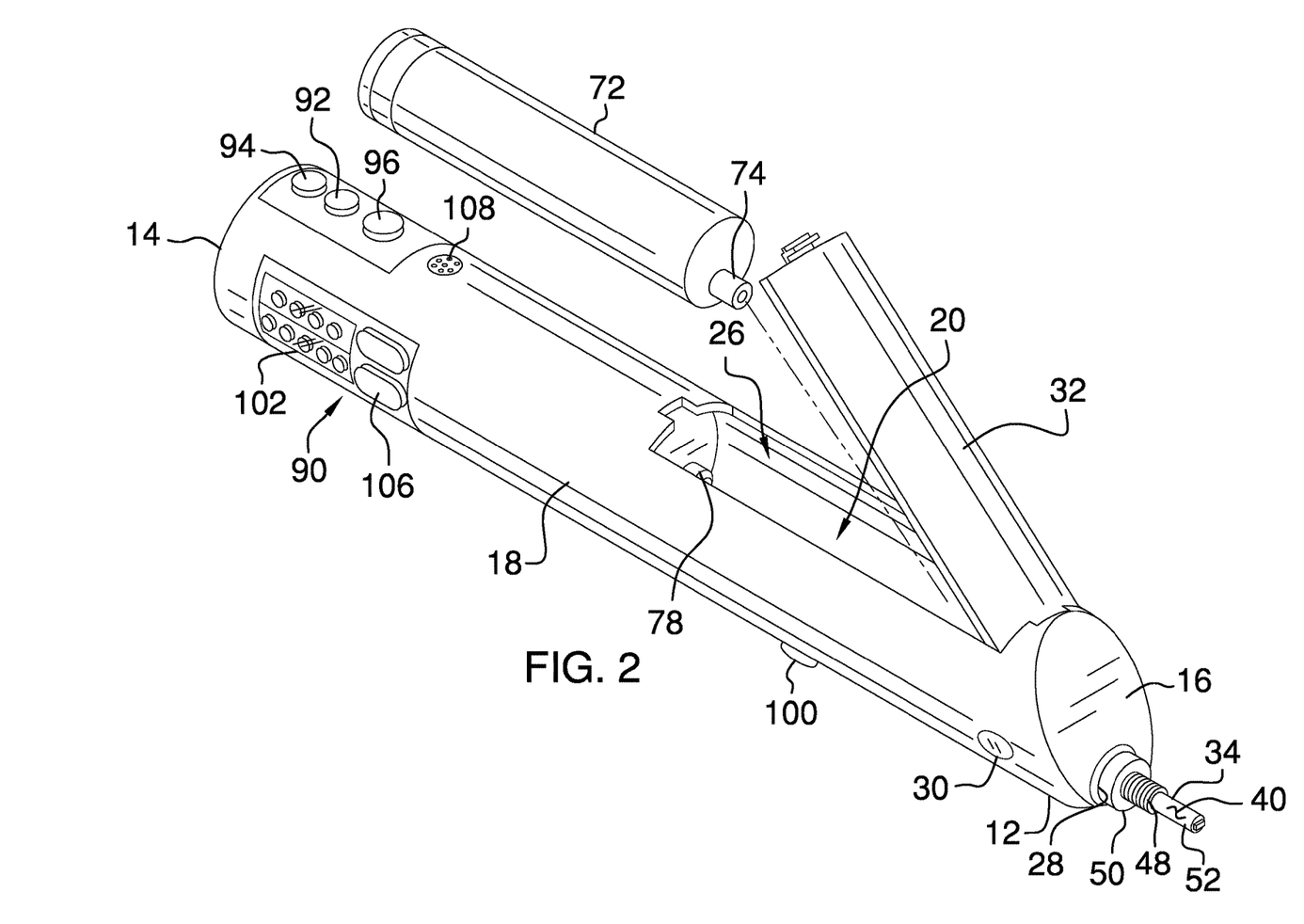
FIG. 2 is an exploded perspective view of an embodiment of the disclosure.
Figure 3:
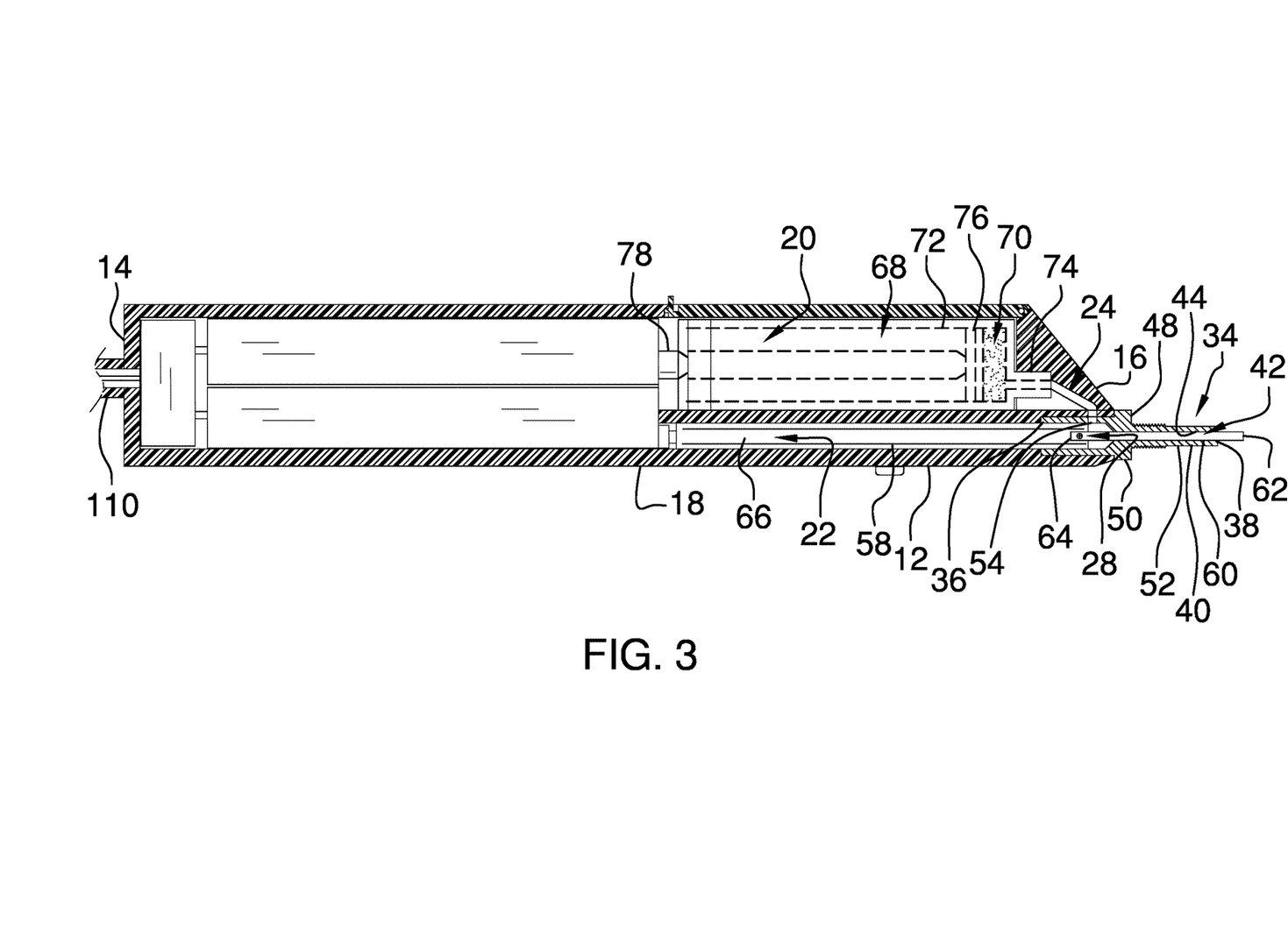
FIG. 3 is a cross sectional view taken along line 3-3 of FIG. 1 of an embodiment of the disclosure.
Figure 4:
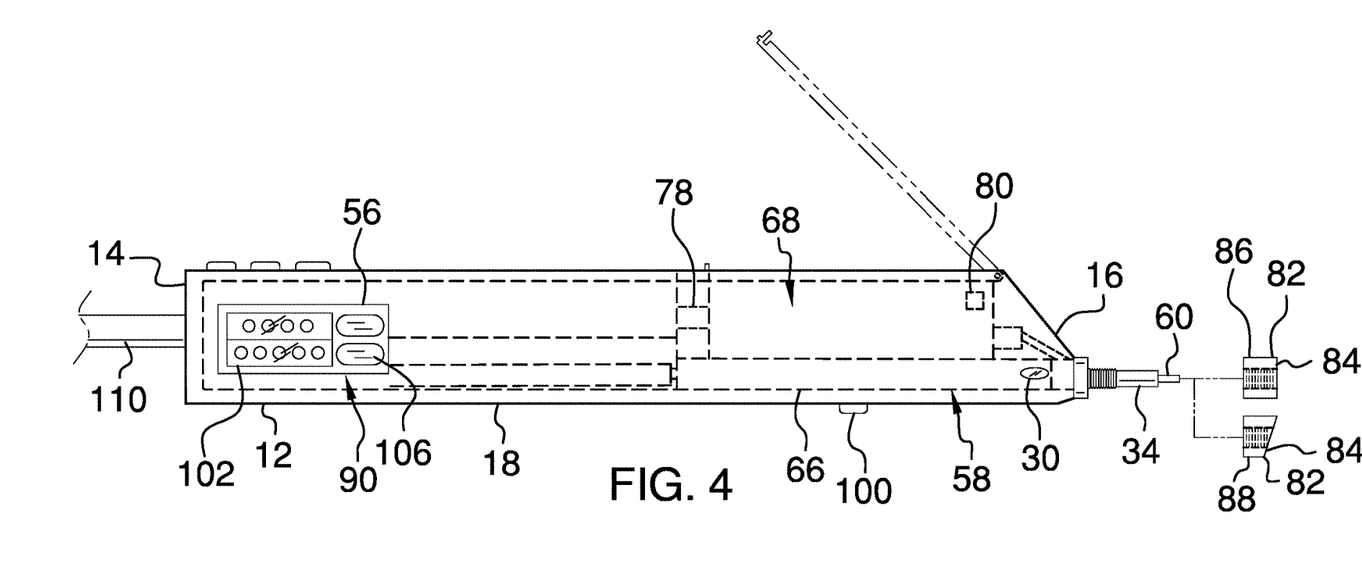
FIG. 4 is a right side phantom view of an embodiment of the disclosure.
Figure 5:
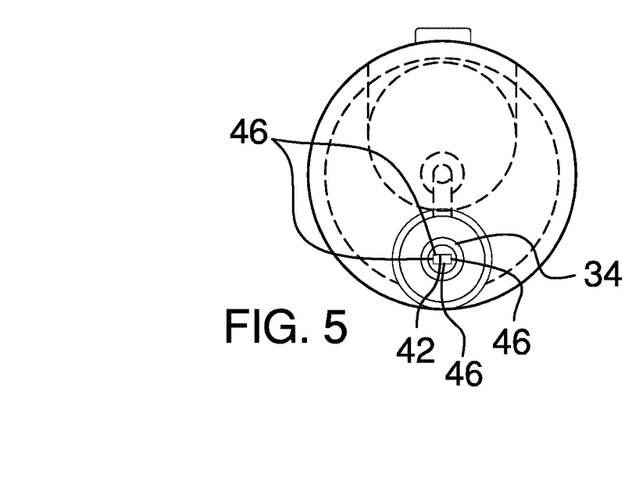
FIG. 5 is a front phantom view of an embodiment of the disclosure.
Figure 6:
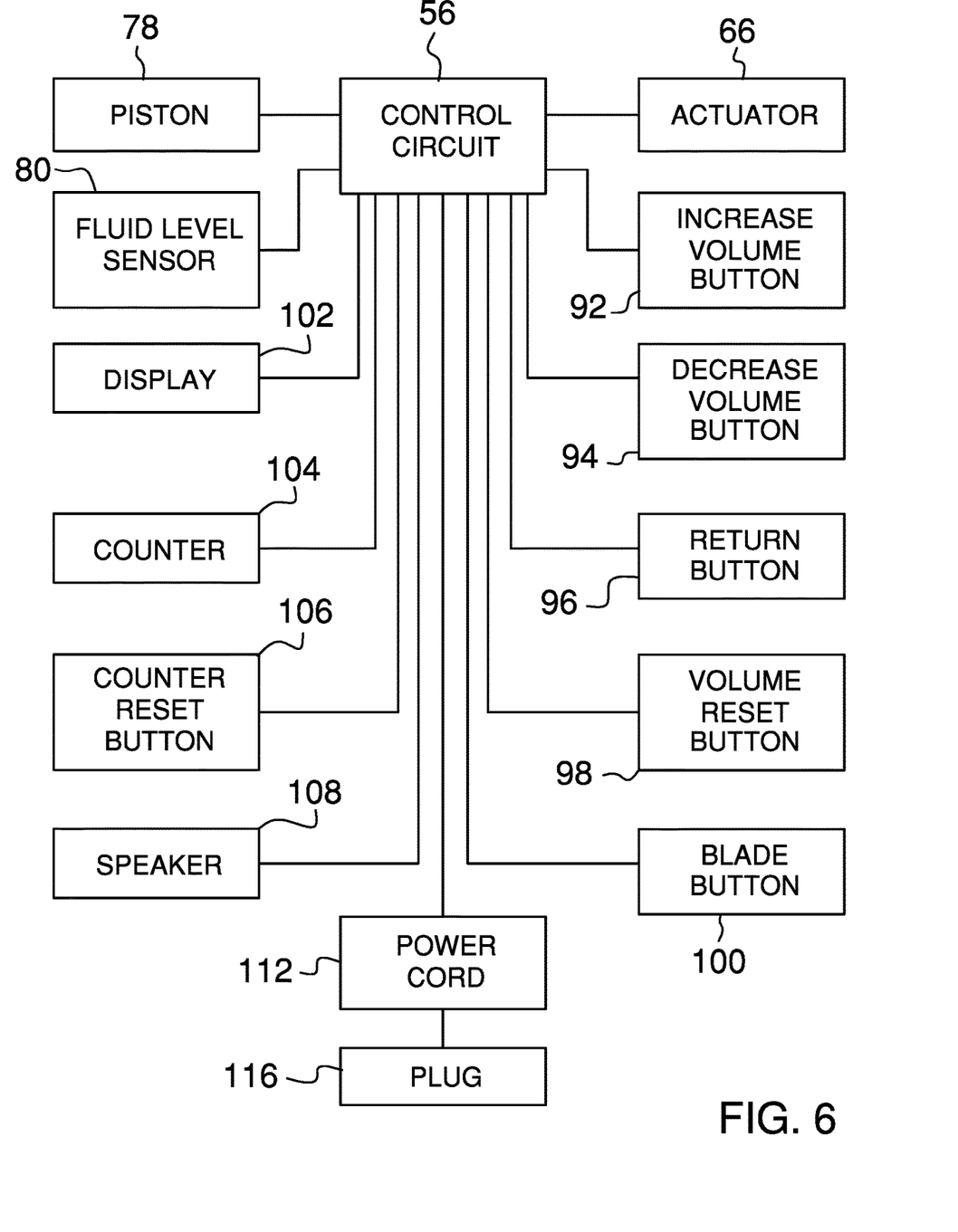
FIG. 6 is a schematic view of an embodiment of the disclosure.

With reference now to the drawings, and in particular to FIGS. 1 through 6 thereof, a new surgical device embodying the principles and concepts of an embodiment of the disclosure and generally designated by the reference numeral 10 will be described.

As best illustrated in FIGS. 1 through 6, the powered hair restoration and surgical assembly 10 generally comprises a housing 12 for gripping during a surgical procedure. The housing 12 has a first end 14, a second end 16 and an outer wall 18 extending therebetween. Additionally, the second end 16 of the housing 12 may be sloped at an angle. The outer wall 18 is continuously arcuate such that the housing 12 has a cylindrical shape and the housing 12 has a cartridge space 20 therein and an blade piston space 22 therein. The housing 12 includes a conduit 24 that is fluidly coupled between the cartridge space 20 and the blade piston space 22. The outer wall 18 has a cartridge opening 26 extending into the cartridge space 20, the second end 16 has a blade opening 28 extending into the blade piston space 22 and the outer wall 18 has a blade window 30 extending therethrough. A cover 32 is removably attached to the housing 12 to close the cartridge opening 26.

A blunt dissector 34 is provided and the blunt dissector 34 is removably coupled to the housing 12 for manipulating an incision. The blunt dissector 34 has a primary end 36, a secondary end 38 and an outer surface 40 extending therebetween. The blunt dissector 34 is elongated between the primary end 36 and the secondary end 38 and the blunt dissector 34 may have a length ranging between approximately 15.0 mm and 40.0 mm. Additionally, the outer surface 40 is continuously arcuate such that the blunt dissector 34 has a tubular shape. The blunt dissector 34 has an aperture 42 extending through the primary end 36 and the secondary end 38 and the aperture 42 has a bounding surface 44. Moreover, the bounding surface 44 has a plurality of intersecting sides 46 such that the aperture 42 has a rectangular shape. The outer surface 40 of the blunt dissector 34 has a vertical portion 48 separating a first half 50 of the blunt dissector 34 from a second half 52 of the blunt dissector 34.

The outer surface 40 corresponding to the first half 50 of the blunt dissector 34 is threaded for threadably engaging a bounding surface 44 of the blade opening 28. The secondary end 38 of the blunt dissector 34 is spaced from the second end 16 of the housing 12 when the blunt dissector 34 is threaded into the blade opening 28. The outer surface 40 corresponding to the second half 52 is threaded adjacent to the vertical portion 48 and the outer surface 40 corresponding to the first half 50 has a hole 54 extending into the aperture 42. Moreover, the hole 54 is aligned with the fluid conduit 24 when the blunt dissector 34 is positioned in the housing 12. In this way the aperture 42 in the blunt dissector 34 is in fluid 70 communication with the cartridge space 20.

A control circuit 56 is provided and the control circuit 56 is positioned in the housing 12. An incising unit 58 is movably positioned in the housing 12 and the incising unit 58 is extendable outwardly through the blunt dissector 34. Thus, the incising unit 58 is selectively positionable to incise skin on a patient during a surgical procedure. The surgical procedure may be a hair restorative implant procedure on a scalp or the like. Additionally, the incising unit 58 is retractable into the blunt dissector 34 thereby facilitating the blunt dissector 34 to bluntly manipulate an incision made by the incising unit 58.

The incising unit 58 comprises a blade 60 that has a first end 62 and a second end 64, and the blade 60 is slidably positioned in the aperture 42 in the blunt dissector 34. The blade 60 has a width that corresponds to a width of the aperture 42 in the blunt dissector 34. The blade 60 is positionable in a cutting position having the first end 62 of the blade 60 being directed outwardly from the secondary end 38 of the blunt dissector 34 for incising. Moreover, the first end 62 of the blade 60 is sharpened for making an incision of a specific length that is equal to the width of the blade 60. In this way the skin on the scalp or the like may be precisely incised for planting a hair follicle transplant thereby enhancing accuracy of the procedure and reducing healing time for the patient. Additionally, the blade 60 is positionable in a retracted position having the first end 62 of the blade 60 being recessed within the secondary end 38 of the blunt dissector 34.

A blade piston 66 is positioned within the blade piston space 22 and the blade piston 66 is electrically coupled to the control circuit 56. The blade piston 66 releasably engages the second end 16 of the blade 60 and the blade piston 66 is turned on to urge the blade 60 between the cutting position and the retracted position. Moreover, the blade piston 66 is aligned with the blade window 30 in the housing 12 such that a coupling between the second end 16 of the blade 60 and the blade piston 66 is visible through the blade window 30. The blade piston 66 may be an electronic linear blade piston or the like or other blade piston that moves back and forth along a longitudinal axis. The coupling between the second end 16 of the blade 60 and the blade piston 66 may comprise a threaded fastener, a push button mechanism and any other releasable fastener that can be manipulated through the blade window 30. Additionally, the coupling between the second end 16 of the blade 60 and the blade piston 66 may be electronically adjustable via electromechanical action of the blade piston 66 or any other conceivable electro-mechanical means of adjusting the coupling.

A fluid dispenser unit 68 is positioned in the housing 12 and the fluid dispenser unit 68 is electrically coupled to the control circuit 56. The fluid dispenser unit 68 contains a fluid 70 comprising saline solution, an anesthetic, surgical ink and any other solution a surgeon sees as essential to the surgical procedure. The fluid dispenser unit 68 is in fluid communication with the incising unit 58 to deliver a selectable volume of the fluid 70 into the incision when the incising unit 58 is extended outwardly through the blunt dissector 34.

The fluid dispenser unit 68 comprises a cartridge 72 that contains the fluid 70. The cartridge 72 is positionable within the cartridge space 20 and the cartridge 72 includes an outlet 74 and a plunger 76. The cartridge may have a fluid volume ranging between approximately 3.0 ml and 5.0 ml. The plunger 76 is slidably positioned within the cartridge 72 and the outlet 74 is fluidly coupled to the fluid conduit 24 when the cartridge 72 is positioned in the cartridge space 20. A gasket or the like may be positioned around the outlet 74 to form a fluid 70 impermeable seal with the conduit 24 when the cartridge 72 is positioned in the cartridge space 20. The fluid 70 in the cartridge 72 is directed through the fluid conduit 24 and outwardly through the aperture 42 in the blunt dissector 34 when the plunger 76 is urged toward the outlet 74. In this way the fluid 70 is selectively released into the incision.

A plunger piston 78 is positioned within the housing 12 and the plunger piston 78 engages the plunger 76. The plunger piston 78 is electrically coupled to the control circuit 56 and the plunger piston 78 is turned on to urge the plunger 76 toward the outlet 74 thereby urging the fluid 70 through the fluid conduit 24. Moreover, the plunger piston 78 is turned on to move a selectable distance toward the outlet 74 when the blade piston 66 is turned on. In this way a selectable volume of the fluid 70 is delivered into the incision. A fluid level sensor 80 is coupled to the cartridge 72 and the fluid level sensor 80 is electrically coupled to the control circuit. The fluid level sensor 80 detects motion of the plunger piston 78 and communicates the distance traveled by the plunger piston 78 to the control circuit 56. Moreover, the control circuit 56 calculates the precise amount of fluid 70 dispensed based upon the distance traveled by the plunger piston 78. The control circuit 56 generates a fluid level low alert when the control circuit 56 determines that the fluid 70 remaining in the cartridge 72 has fallen below a predetermined minimum volume. The plunger piston 78 may be an electrically driven piston or the like and the fluid level sensor 80 may be an electronic motion sensor or the like.

A pair of collars 82 is provided and a selected one of the collars 82 is positioned around the blunt dissector 34 and threadably engages the outer surface 40 corresponding to the second half 52 of the blunt dissector 34. Moreover, each of the collars 82 has a diameter that is significantly larger than a diameter of the blunt dissector 34. Each of the collars 82 has a first surface 84 and the first surface 84 of the selected collar is spaceable a selected distance from the secondary end 38 of the blunt dissector 34. Thus, the first surface 84 of the selected collar 82 abuts the skin of the patient for controlling a depth of the incision.

The pair of collars 82 includes a first collar 86 and a second collar 88. The first surface 84 corresponding to the first collar 86 lies on a plane oriented perpendicular to an axis extending through the primary end 36 and the secondary end 38 of the blunt dissector 34 when the first collar 86 is positioned on the blunt dissector 34. Thus, the first collar 86 orients the blade 60 at a perpendicular angle with respect to the patient's skin when the first collar 86 abuts the patient's skin. The first surface 84 corresponding to the second collar 88 lies on a plane oriented at an acute inside angle with the axis when the second collar 88 is positioned on the blunt dissector 34. Thus, the second collar 88 orients the blade 60 at an acute angle with respect to the patient's skin when the second collar 88 abuts the patient's skin.

A control 90 is positioned on the housing 12 and the control 90 is electrically coupled to the control circuit 56. The control 90 controls the operational parameters of the incising unit 58 and the fluid dispenser unit 68. The control 90 comprises an increase volume button 92 that is movably coupled to the housing 12. The increase volume button 92 is in electrical communication with the plunger piston 78 to increase the distance the plunger piston 78 moves. In this way a volume of fluid 70 dispensed each time the plunger piston 78 moves is increased in an increment of approximately 0.1 ml.

A decrease volume button 94 is movably coupled to the housing 12. The decrease volume button 94 is in electrical communication with the plunger piston 78 to decrease the distance the plunger piston 78 moves when the blade piston 66 is turned on. In this way the volume of fluid 70 dispensed each time the plunger piston 78 moves is decreased in an increment of approximately 0.1 ml. The control circuit 56 calculates the remaining volume of fluid 70 in the cartridge when either of the increase 92 or decrease 94 volume buttons is manipulated. A return button 96 is movably coupled to the housing 12 and the return button 96 is in electrical communication with the plunger piston 78. The plunger piston 78 fully retracts when the return button 96 is manipulated thereby facilitating the cartridge 72 to be removed from the cartridge space 20. A volume reset button 98 is movably coupled to the housing 12 and the volume reset button 98 is in electrical communication with the plunger piston 78. The volume reset button 98 resets the plunger piston 78 to move a default distance to dispense a default volume of the fluid 70 each time the plunger piston 78 moves.

A blade button 100 is movably coupled to the housing 12 and the blade button 100 is in electrical communication with the blade piston 66. The control circuit 56 receives a first input each time the blade button 100 is manipulated. Moreover, the control circuit 56 turns on the blade piston 66 to urge the blade 60 between the cutting position and the retracted position each time the control circuit 56 receives the first input. The blade 60 is in the cutting position for approximately 20.0 milliseconds to 50.0 milliseconds. Additionally, the control circuit 56 turns the plunger piston 78 on each time the control circuit 56 receives the first input and the plunger piston 78 moves the selected distance for releasing the selected volume of fluid 70.

A display 102 is coupled to the outer wall 18 of the housing 12 and the display 102 displays indicia corresponding to the level of fluid 70 sensed by the fluid level sensor 80. Moreover, the display 102 displays all operational parameters of the blade piston 66 and the plunger piston 78, including but not being limited to, the selected distance the plunger piston 78 moves, a duration of time the blade 60 is in the cutting position, the remaining fluid volume in the cartridge 72 and the number of incisions made. The display 102 includes a counter 104 that displays a number of times the blade button 100 has been manipulated.

The control 104 includes a counter reset button 106 that is movably coupled to the housing 12. The counter reset button 106 is in electrical communication with the counter 104 in the display 102 to reset a number of times the blade button 100 has been manipulated to zero. A speaker 108 is coupled to the housing 12 for emitting an alert comprising audible sound and the speaker 108 is in electrical communication with the control circuit 56. The speaker 108 is turned on when the control circuit 56 calculates the fluid 70 in the cartridge 72 has fallen below the pre-determined minimum amount for alerting a user that the cartridge 72 is becoming emptied of the fluid 70.

A power supply 110 is coupled to the housing 12 and the power supply 110 is electrically coupled to the control circuit 56. The power supply 110 comprises a power cord 112 extending outwardly from the housing 12. The power cord 112 has a distal end 114 with respect to the housing 12 and a plug 116 is electrically coupled to the distal end 114. The plug 116 may be electrically coupled to a power source, such a female electrical outlet or the like.

In use, the cartridge 72 is loaded into the cartridge space 20 and the cover 32 is positioned on the housing 12. The selected collar 82 is threaded onto the blunt dissector 34 and the selected collar 82 is positioned at a selected point along the blunt dissector 34. The blunt dissector 34 is positioned against the patient's skin and the blade button 100 is depressed. The blade piston 66 urges the blade 60 between the cutting position and the retracted position thereby incising the patient's skin beneath the blunt dissector 34. Thus, the blunt dissector 34 may be inserted into the incision for spreading the incision for hair follicle transplantation or the like. Moreover, the selected collar 82 ensures the incision does not exceed a predetermined depth thereby reducing trauma to underlying blood vessels and nerves. The plunger piston 78 moves forward the selected distance when the blade 60 has been retracted into the blunt dissector 34 to dispense the selected volume of fluid 70 into the incision.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A powered hair restoration and surgical assembly being configured to incise, bluntly dissect and inject a fluid into an incision, said assembly comprising:

a housing for gripping during a surgical procedure, said housing having a first end, a second end and an outer wall extending therebetween, said outer wall being continuous such that said housing has a cylindrical shape, said housing having a cartridge space therein and an blade piston space therein, said housing having a conduit being fluidly coupled between said cartridge space and said blade piston space, said outer wall having a cartridge opening extending into said cartridge space, said second end having a blade opening extending into said blade piston space, said outer wall having a blade window extending therethrough;

a blunt dissector being removably coupled to said housing wherein said blunt dissector is configured to manipulate an incision, said blunt dissector having a primary end, a secondary end and an outer surface extending therebetween, said blunt dissector having an aperture extending through said primary end and said secondary end, said outer surface having a vertical portion separating a first half of said blunt dissector from a second half of said blunt dissector, said outer surface corresponding to said first half being threaded to threadably engage a bounding surface of said blade opening having said secondary end being spaced from said second end of said housing, said outer surface corresponding to said second half being threaded adjacent to said vertical portion, said outer surface corresponding to said first half having a hole extending into said aperture, said hole being aligned with said fluid conduit when said blunt dissector is positioned in said housing such that said aperture is in fluid communication with said cartridge space;

a control circuit being positioned in said housing;

an incising unit being movably positioned in said housing, said incising unit being extendable outwardly through said blunt dissector wherein said incising unit is configured to incise skin on a patient, said incising unit being retractable into said blunt dissector, said incising unit comprising:
  a blade having a first end and a second end, said blade being slidably positioned in said aperture in said blunt dissector, said first end being sharpened for making an incision of a specific length, said blade being positionable in a cutting position having said first end being directed outwardly from said secondary end of said blunt dissector for incising, said blade being positionable in a retracted position having said first end being recessed within said secondary end of said blunt dissector; and
  an blade piston being positioned within said blade piston space, said blade piston being electrically coupled to said control circuit, said blade piston releasably engaging said second end of said blade, said blade piston being turned on to urge said blade between said cutting position and said retracted position, said blade piston being aligned with said blade window in said housing such that a coupling between said second end of said blade and said blade piston is visible through said blade window;

a fluid dispenser unit being positioned in said housing, said fluid dispenser unit being electrically coupled to said control circuit, said fluid dispenser unit being in fluid communication with said incising unit to deliver a selectable volume of a said fluid into the incision when said incising unit is extended outwardly through said blunt dissector, said fluid dispenser unit comprising:
  a cartridge containing said fluid, said cartridge being positionable within said cartridge space, said cartridge having an outlet and a plunger being positioned within said cartridge, said outlet being fluidly coupled to said fluid conduit when said cartridge is positioned in said cartridge space, said fluid being directed through said fluid conduit and outwardly through said aperture in said blunt dissector when said plunger is urged toward said outlet wherein said fluid is configured to be released into the incision;
  a plunger piston being positioned within said housing, said plunger piston engaging said plunger, said plunger piston being electrically coupled to said control circuit, said plunger piston being turned on to urge said plunger toward said outlet to urge said fluid through said fluid conduit, said plunger piston being turned on to move a selectable distance toward said outlet when said blade piston is turned on for delivering a selectable volume of said fluid into the incision; and
  a fluid level sensor being coupled to said cartridge, said fluid level sensor being electrically coupled to said control circuit, said fluid level sensor detecting motion of said plunger piston and communicating the distance traveled by said plunger piston to said control circuit, said control circuit calculating the precise amount of fluid dispensed based upon the distance traveled by said plunger piston, said control circuit generating a fluid level low alert when said control circuit determines that the fluid remaining in said cartridge has fallen below a predetermined minimum volume;

a pair of collars, a selected one of said collars being positioned around said blunt dissector and threadably engaging said outer surface corresponding to said second half of said blunt dissector, each of said collars having a first surface, said first surface of said selected collar being spaceable a selected distance from said secondary end of said blunt dissector wherein said first surface of said selected collar is configured to abut the skin of the patient for controlling a depth of the incision, said pair of collars including a first collar and a second collar, said first surface corresponding to said first collar lying on a plane being oriented perpendicular to an axis extending through said primary end and said secondary end of said blunt dissector when said first collar is positioned on said blunt dissector wherein said first collar is configured to orient said blade at a perpendicular angle with respect to the patient's skin, said first surface corresponding to said second collar lying on a plane being oriented at an acute inside angle with said axis when said second collars positioned on said blunt dissector wherein said second collar is configured to orient said blade at an acute angle with respect to the patient's skin;

a control being positioned on said housing, said control being electrically coupled to said control circuit for controlling operational parameters of said incising unit and said fluid dispenser unit, said control comprising:
  an increase volume button being movably coupled to said housing, said increase volume button being in electrical communication with said plunger piston to increase the distance said plunger piston moves;
  a decrease volume button being movably coupled to said housing, said decrease volume button being in electrical communication with said plunger piston to decrease the distance said plunger piston moves;
  a return button being movably coupled to said housing, said return button being in electrical communication with said plunger piston, said plunger piston fully retracting when said return button is manipulated;

a blade button being movably coupled to said housing, said blade button being in electrical communication with said blade piston, said control circuit receiving a first input each time said blade button is manipulated, said control circuit turning said blade piston on blade piston to urge said blade between said cutting position and said retracted position each time said control circuit receives said first input, said control circuit turning said plunger piston on each time said control circuit receives said first input;

a display being coupled to said outer wall of said housing, said display displaying indicia corresponding to said a level of fluid sensed by said fluid level sensor, said display including a counter displaying a number of times said blade button has been manipulated;

a volume reset button being movably coupled to said housing, said volume reset button being in electrical communication with said plunger piston, said volume reset button resetting said plunger piston to move a default distance;

a counter reset button being movably coupled to said housing, said counter reset button being in electrical communication with said counter in said display to reset a number of times said blade button has been manipulated to zero; and a speaker being coupled to said housing for emitting an alert comprising audible sounds, said speaker being in electrical communication with said control circuit, said speaker being turned on when said control circuit calculates the volume of said fluid in said cartridge has fallen below a pre-determined minimum amount for alerting a user that said cartridge is becoming emptied of said fluid; and a power supply being coupled to said housing, said power supply being electrically coupled to said control circuit, said power supply comprising a power cord extending outwardly from said housing, said power cord having a distal end with respect to said housing, said distal end having a plug being electrically coupled thereto, said plug being configured to be electrically coupled to a power source.

* * * * *